(12) United States Patent
Fenaroli et al.

(10) Patent No.: US 6,361,538 B1
(45) Date of Patent: **\*Mar. 26, 2002**

(54) METHOD FOR TREATING ORTHOPEDIC FRACTURES WITH A FIXATION MEMBER

(75) Inventors: Don Fenaroli, Lake Elsinore, CA (US); Roy W. Sanders, Tampa, FL (US); G. Bryan Cornwall, San Diego, CA (US)

(73) Assignee: DePuy Orthopaedics, Inc., Warsaw, IN (US)

(\*) Notice: Subject to any disclaimer, the term of this patent is extended or adjusted under 35 U.S.C. 154(b) by 0 days.

This patent is subject to a terminal disclaimer.

(21) Appl. No.: 09/812,303

(22) Filed: Mar. 20, 2001

Related U.S. Application Data (63) Continuation of application No. 09/495,138, filed on Jan. 31, 2000, now Pat. No. 6,228,087.

(51) Int. Cl.⁷ .............................................. A61B 17/56
(52) U.S. Cl. ........................... 606/73; 606/69; 606/104
(58) Field of Search ........................... 606/69, 70, 73, 606/72, 75, 104; 411/89, 132, 338

(56) References Cited

U.S. PATENT DOCUMENTS

| | | | |
|---|---|---|---|
| 173,385 A | * 2/1876 | Adgate | 606/73 |
| 2,355,986 A | 8/1944 | MacLean, Jr. et al. | |
| 2,511,051 A | * 6/1950 | Dzus | 606/69 |
| 3,939,498 A | 2/1976 | Lee et al. | |
| 4,279,249 A | 7/1981 | Vert et al. | |
| 4,364,382 A | 12/1982 | Mennen | |
| 4,651,724 A | * 3/1987 | Berentey et al. | 606/73 |
| 4,802,477 A | 2/1989 | Gabbay | |
| 5,006,120 A | 4/1991 | Carter | |
| 5,053,036 A | 10/1991 | Perren et al. | |
| 5,147,361 A | 9/1992 | Ojima et al. | |
| 5,201,737 A | 4/1993 | Leibinger et al. | |
| 5,269,784 A | 12/1993 | Mast | |
| 5,707,373 A | 1/1998 | Sevrain et al. | |
| 5,718,705 A | 2/1998 | Sammarco | |
| 6,228,087 B1 | * 5/2001 | Fenaroli et al. | 606/73 |

\* cited by examiner

*Primary Examiner*—Pedro Philogene
(74) *Attorney, Agent, or Firm*—Maginot, Moore & Bowman (57) ABSTRACT

A method of inhibiting relative movement between a first bone fragment and a second bone fragment is disclosed. The method includes the step of advancing a fastener into the second bone fragment, the advancing step causing the fastener to contact a fixation member which in turn causes a first penetration structure of the fixation member to penetrate through an outer surface of the first bone fragment. The method further includes the step of preventing further advancement of the penetration structure into the first bone fragment with a stop member of the fixation member so that a space is maintained between a lower surface of a body of the fixation member and the outer surface of the first bone fragment.

20 Claims, 4 Drawing Sheets

METHOD FOR TREATING ORTHOPEDIC FRACTURES WITH A FIXATION MEMBER

This application is a continuation of application Ser. No. 09/495,138, filed on Jan. 31, 2000, now U.S. Pat. No. 6,228,087.

BACKGROUND OF THE INVENTION

The present invention generally relates to a method for treating orthopedic injuries or disease. The present invention particularly relates to a method which utilizes a fixation member configured to be utilized in orthopedic surgery for the treatment of periarticular orthopedic fractures.

Physicians utilize various appliances to treat orthopedic conditions or injuries. For example, a periarticular plate is one type of appliance employed by physicians to treat certain types of orthopedic injuries. In particular, periarticular plates are used during orthopaedic surgery to engage and stabilize comminuted bone. Periarticular plates can also be used to distribute a load in osteopenic bone.

Typically, periarticular plates are configured as flat pieces of titanium, surgical grade stainless steel, or other surgical grade alloys. In addition, a periarticular plate will typically have multiple holes defined therein such that the periarticular plate can be secured to a piece of bone and/or bone fragments with a number of screws. Once attached to comminuted bone in the above described manner, the periarticular plate functions to inhibit relative movement between bone fragments and thus enhances healing.

While periarticular plates enhance the healing of comminuted bone to some degree, they also suffer from a number of drawbacks. For example, once attached to the bone, the flat "plate like" nature of these appliances result in a relatively large surface area of the periarticular plate being biased against the damaged bone. Having a relatively large surface area of the periarticular plate biased against the damaged bone can occlude or otherwise inhibit blood flow to some areas of the bone and thus delay healing. In extreme cases, necrosis may result from the aforementioned occlusion. In addition, the flat "plate like" configuration of periarticular plates results in these appliances having a somewhat limited ability to actually inhibit the relative movement between bone fragments. The use of multiple screws to attach the periarticular plate to the bone fragments helps to alleviate the aforementioned problem, however, in many instances the bone fragments are too small or brittle to withstand the insertion of one or more screws.

Therefore, there is a need for a method for treating periarticular orthopedic fractures which addresses one or more of the above described drawbacks.

SUMMARY OF THE INVENTION

In accordance with one embodiment of the present invention, there is provided a fixation member for treating orthopedic fractures. The fixation member includes a body portion having (i) an upper surface, (ii) a lower surface, and (iii) a perimeter edge interposed between the upper surface and the lower surface. The fixation member also includes a number of arm members each having a first end and a second end. The first end of each arm member being secured to the perimeter edge such that each arm member extends in a radial direction relative to the body portion. The fixation member further includes a penetration structure secured to the second end of each arm member such that each penetration structure extends in an axial direction relative to the body portion. The penetration structure is configured so as to penetrate below an outer surface of a bone when the fixation member is biased against the outer surface of the bone. The penetration structure is further configured to limit the penetration so that the lower surface of the body portion is prevented from contacting the outer surface of the bone when the fixation member is biased against the outer surface of the bone.

Pursuant to another embodiment of the present invention, there is provided a fixation member for treating orthopedic fractures. The fixation member includes a body portion having (i) an upper surface, (ii) a lower surface, (iii) a perimeter edge interposed between the upper surface and the lower surface, and (iv) a fastener hole defined therein. The fixation member also includes a number of arm members each having a first end and a second end, the first end of each arm member being secured to the perimeter edge such that (i) each arm member extends in a radial direction relative to a perpendicular central axis of the body portion and (ii) the arm members are spaced apart from one another along the perimeter edge such that a notch is defined between adjacent arm members. The fixation member also includes a penetration structure secured to each arm member such that each penetration structure extends in an axial direction relative to the perpendicular central axis of the body portion. Each penetration structure is (i) configured so as to penetrate below an outer surface of a bone when the fixation member is biased against the outer surface of the bone and (ii) further configured to limit the penetration so that the lower surface of the body portion is prevented from contacting the outer surface of the bone when the fixation member is biased against the outer surface of the bone.

Pursuant to yet another embodiment of the present invention there is provided a fixation member for treating orthopedic fractures. The fixation member includes a body portion having (i) an upper surface, (ii) a lower surface, (iii) a perimeter edge interposed between the upper surface and the lower surface, and (iv) a fastener hole defined therein. The fixation member also includes a first arm member having a length $L_1$. The first arm member is secured to the perimeter edge such that the first arm member extends in a radial direction relative to the body portion. The fixation member also includes a second arm member having a length $L_2$ which is greater than length $L_1$. The second arm member is secured to the perimeter edge such that the second arm member extends in a radial direction relative to the body portion. The fixation member further includes a first penetration structure secured to the first arm member such that the first penetration structure extends in an axial direction relative to the body portion. The fixation member also includes a second penetration structure secured to the second arm member such that the second penetration structure extends in an axial direction relative to the body portion. The first penetration structure and the second penetration structure are both configured so as to penetrate below an outer surface of a bone when the fixation member is biased against the outer surface of the bone. The first penetration structure and the second penetration structure are both further configured to limit the penetration so that the lower surface of the body portion is prevented from contacting the outer surface of the bone when the fixation member is biased against the outer surface of the bone.

Pursuant to still another embodiment of the present invention there is provided a fixation member for treating orthopedic fractures. The fixation member includes a body portion having (i) an upper surface, (ii) a lower surface, and (iii) a perimeter edge interposed between the upper surface and the lower surface. The fixation member also includes a number of arms secured to and extending outward from the perimeter edge of the body portion in a radial direction. The fixation member also includes a penetration structure secured to each of the arm members such that each penetration structure extends in an axial direction relative to the body portion. Each of the penetration structures is configured so as to penetrate below an outer surface of a bone when the fixation member is biased against the outer surface of the bone. The fixation member also includes a stop member connected to the body portion. The stop member is configured to limit the penetration of the penetration structures so that the lower surface of the body portion is prevented from contacting the outer surface of the bone when the fixation member is biased against the outer surface of the bone.

Pursuant to yet another embodiment of the present invention there is provided a fixation member for treating orthopedic fractures. The fixation member includes a body portion and a number of arm members secured to and extending outward from the body portion. The fixation member also includes a penetration structure secured to each of the arm members which is configured to penetrate below an outer surface of a bone when the fixation member is biased against the outer surface of the bone. The fixation member further includes a stop member connected to the body portion. The stop member is configured to limit the penetration of the penetration structures when the fixation member is biased against an outer surface of the bone.

It is therefore an object of the present invention to provide a new and useful apparatus for treating orthopedic injuries or disease.

It is another object of the present invention to provide an improved apparatus for treating orthopedic injuries or disease.

It is still another object of the present invention to provide a new and useful fixation member configured to be utilized in orthopedic surgery for the treatment of orthopedic fractures.

It is another object of the present invention to provide an improved fixation member configured to be utilized in orthopedic surgery for the treatment of orthopedic fractures.

It is also an object of the present invention to provide a fixation member configured to be utilized in orthopedic surgery for the treatment of orthopedic fractures which does not inhibit the flow of blood to damaged bone.

It is still another object of the present invention to provide a fixation member configured to be utilized in orthopedic surgery for the treatment of orthopedic fractures which effectively inhibits the relative movement between bone fragments of comminuted bone.

The above and other objects, features, and advantages of the present invention will become apparent from the following description and attached drawings.

DETAILED DESCRIPTION OF THE PREFERRED EMBODIMENT

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 1:
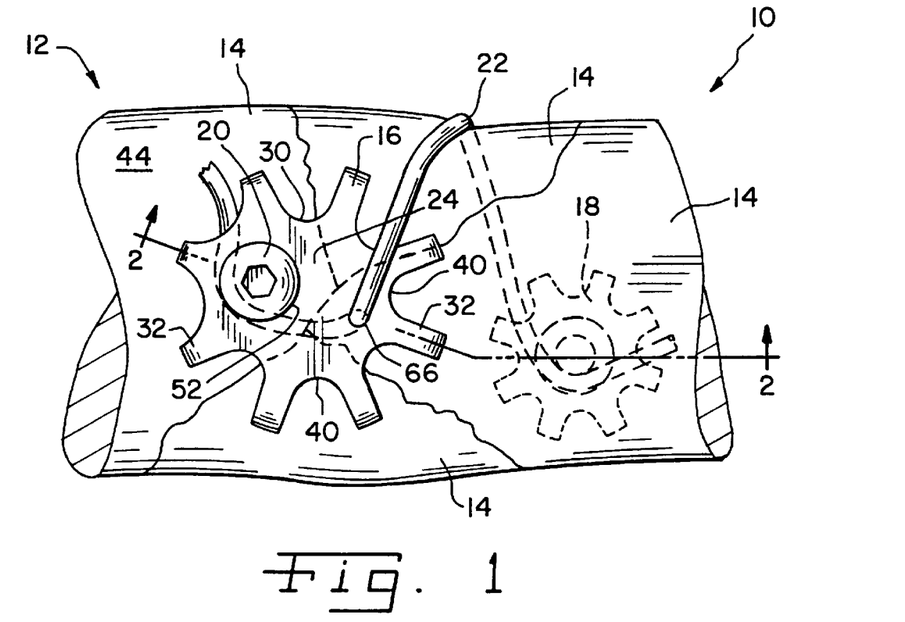
FIG. 1 is an elevational view of an apparatus which incorporates the features of the present invention therein attached to a segment of comminuted bone (note that portions of the apparatus are shown in phantom for clarity of description)
Figure 2:
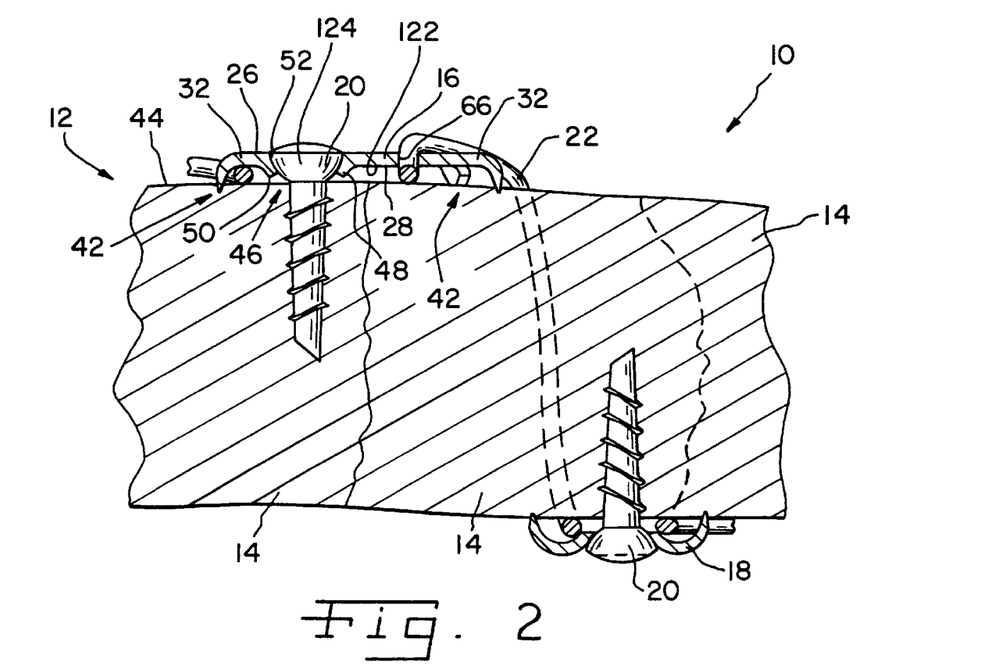
FIG. 2 is a cross-sectional view of the apparatus and bone segment taken along the line 2—2 of FIG. 1 as viewed in the direction of the arrows.

Referring to FIGS. 1 and 2, there is shown an apparatus 10 which incorporates the features of the present invention therein. As discussed in greater detail below, apparatus 10 can be utilized to immobilized bone fragments 14 of a comminuted bone 12 (hereinafter referred to as bone 12). In the exemplary embodiment of apparatus 10 shown in FIGS. 1 and 2, apparatus 10 includes a fixation member 16, a fixation member 18, screws 20, and a k-wire 22.

As shown more clearly shown in FIGS. 9, 10, 11, and 15, fixation member 16 includes a number of arm members 32, a stop member 46, penetration structures 42, and a body portion 24. Body portion 24 has a fastener hole 52 and a wire hole 66 defined therein. Body portion 24 also has an upper surface 26, a lower surface 28, and a perimeter edge 30 interposed between upper surface 26 and lower surface 28. It should be understood that while body portion 24 is shown as being substantially annular shaped, other shapes are contemplated. For example, body portion 24 could be square shaped or have an oblong shape.

Figure 10:
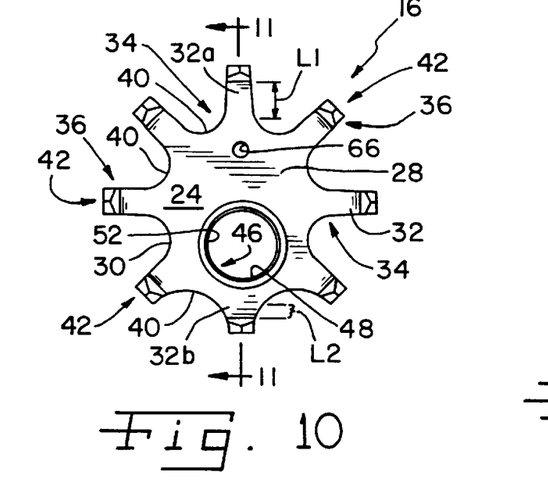
FIG. 10 is a bottom elevational view of the fixation member of FIG. 9.
Figure 11:
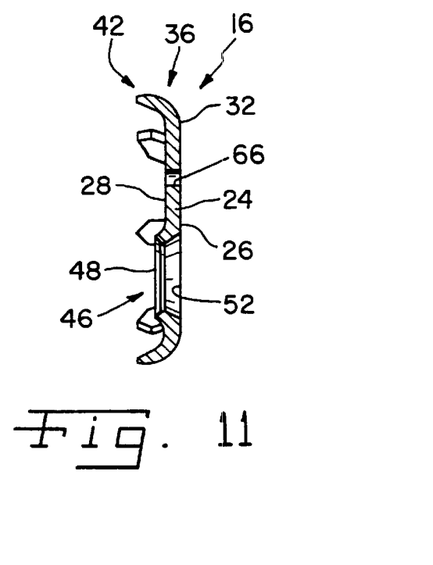
FIG. 11 is a cross-sectional view taken along the line 11—11 of FIG. 10 as viewed in the direction of the arrows.

Still referring to FIGS. 9, 10, 11, and 15, each arm member 32 has an end 34 secured to perimeter edge 30 of body portion 24 so that each arm member 32 extends outwardly in a radial direction relative to a perpendicular central axis 38 of body portion 24. Moreover, arm members 32 are spaced apart from one another along perimeter edge 30 such that a notch 40 is defined between adjacent arm members 32. It should be appreciated that arm members 32 can have various lengths. For example, as shown in FIG. 10, arm member 32a has a length $L_1$ which is greater than the length $L_2$ of arm member 32b. Having arm members 32 of various lengths is an advantage of the present invention since it enhances the ability of fixation member 16 to reach and stabilize a greater surface area of comminuted bone 12 (see FIG. 1). In other words, the aforementioned advantage allows arm members 32 of fixation member 16 to reach, contact, and thus and stabilize, a greater number of bone fragments 14 (see FIGS. 1 and 2) in comminuted bone 12.

It should be understood that fixation member 16 (including arm members 32) is preferably made from a material having a relatively low elastic modulus. For example, fixation member 16 can be made from titanium. Having fixation member 16 made from a low elastic modulus material allows fixation member 16 to slightly bend or flex when biased against an outer surface 44 of bone 12 with a fastener, such as screw 20 (see FIGS. 1 and 2). In addition, it should be understood that the above described notches 40 enhance the ability of arm members 32 to slightly bend or flex and thus further allow fixation member 16 to readily conform to the irregular surface features of bone 12. The above described ability to slightly flex allows fixation member 16 to readily conform to the irregular surface features of bone 12 and thus exert an equal pressure on outer surface 44 when biased against bone 12 with screw 20. Moreover, the ability of fixation member 16 to slightly bend under a load ensures that penetration structures 42 remains in contact with bone 12 and thus substantially prevent relative movement between bone fragments 14.

Figure 15:
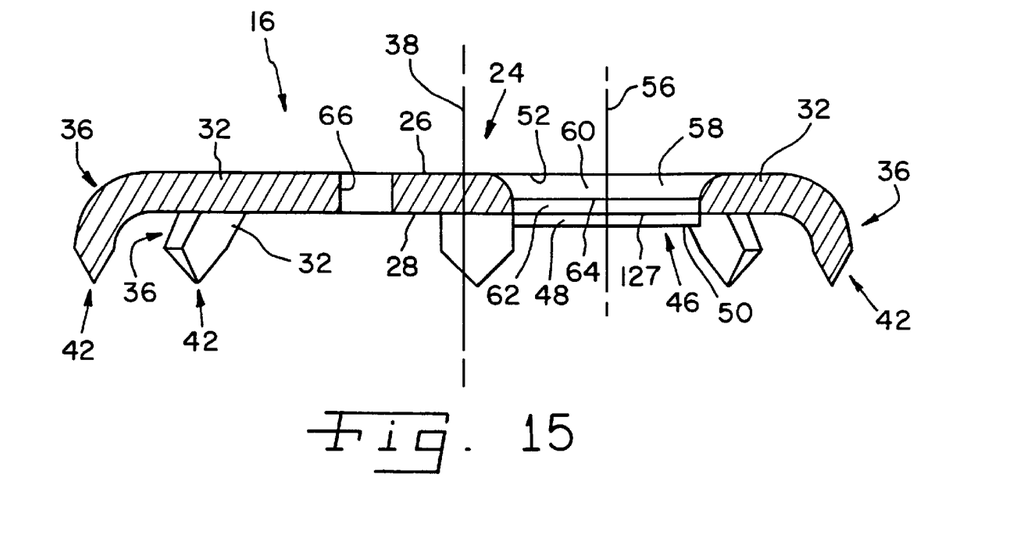
FIG. 15 is an enlarged view of FIG. 11.
Figure 16:
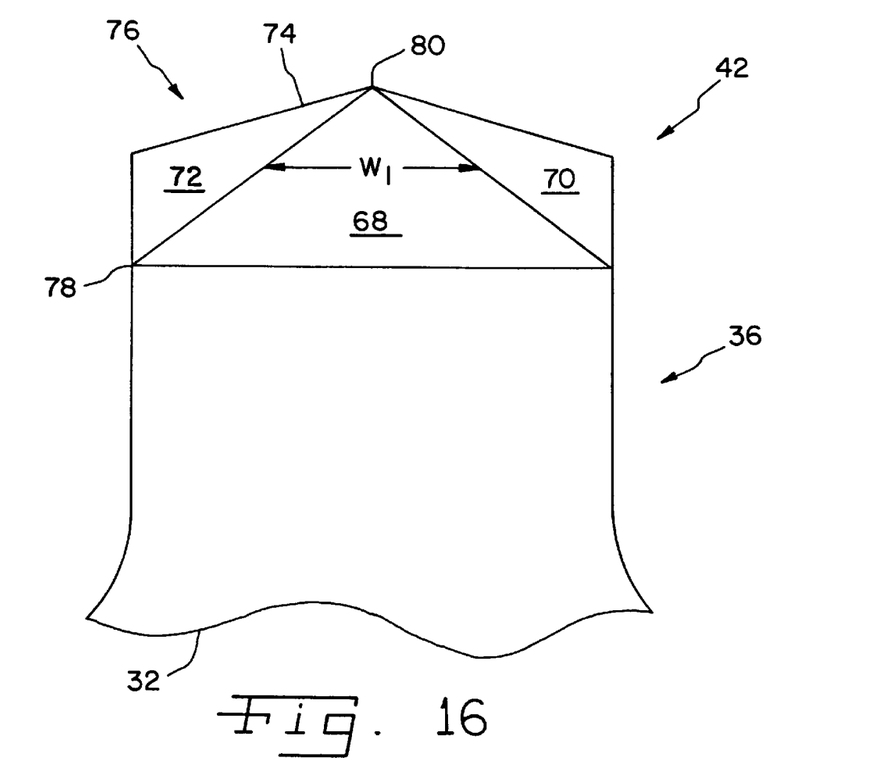
FIG. 16 is an enlarged perspective view of a penetration structure.
Figure 17:
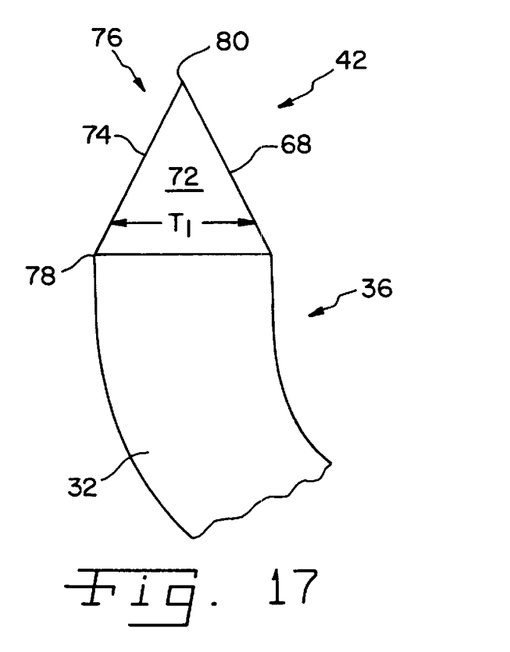
FIG. 17 is an enlarged side elevational view of a penetration structure.

As shown more clearly in FIGS. 15, 16, and 17, a penetration structure 42 is secured to an end 36 of each arm member 32 such that each penetration structure 42 extends in an axial direction relative to perpendicular central axis 38 of body portion 24. Each penetration structure 42 is configured so as to penetrate below outer surface 44 of bone 12 when fixation member 16 is biased against outer surface 44 of bone 12. In addition, each penetration structure 42 is further configured so as to limit the aforementioned penetration such that lower surface 28 of body portion 24 is prevented from contacting outer surface 44 of bone 12 (see FIGS. 1 and 2) when fixation member 16 is biased against outer surface 44 of bone 12.

Each penetration structure 42 is configured to be defined by substantially triangular shaped wall segments 68, 70, 72, and 74. In particular, substantially triangular shaped wall segments 68, 70, 72, and 74 are secured together so as to form a pyramid structure 76 having a base 78 and an apex 80. Pyramid structure 76 has a width $W_1$ (see FIG. 16) and a thickness $T_1$ (see FIG. 17). It should be appreciated that width $W_1$ and thickness $T_1$ of pyramid structure 76 both increase moving along the direction from apex 80 to base 78. Having the width W. and the thickness $T_1$ of pyramid structure 76 increase from apex 80 to base 78 serves two purposes. First, this configuration functions to allow each penetration structure 42 to penetrate below outer surface 44 of bone 12 to a certain degree when fixation member 16 is biased against outer surface 44 of bone 12. Second, the aforementioned configuration also functions to limit the amount each penetration structure 42 can penetrate below outer surface 44 of bone 12. In particular, as a penetration structure 42 is urged against outer surface 44 of bone 12 (for example with screw 20), apex 80 of pyramid structure 76 is advanced through outer surface 44 so as to create a hole (not shown) therein. As penetration structure 42 is further urged against outer surface 44, penetration structure 42 becomes embedded in, or penetrates into, bone 12 such that a portion of each substantially triangular shaped wall segment 68, 70, 72, and 74 comes into contact with bone tissue. However, since width $W_1$ and thickness $T_1$ of pyramid structure 76 increase from apex 80 to base 78, an increasing amount of force is required to further advance penetration structure 42 into bone 12. This force continues to increase as penetration structure 42 is advanced further into bone 12 until the force required to still further advance penetration structure 42 into bone 12 approaches a point that exceeds the amount of force capable of being realistically generated by the biasing mechanism (e.g. screw 20). Once the force begins to approach the aforementioned point, the advancement of penetration structure 42 into bone 12 stops. It should be understood that penetration structures 42 are constructed so that the point where they can no longer be advanced into bone 12 occurs well before lower surface 26 comes into contact with bone 12. Therefore, it should be appreciated that limiting the amount each penetration structure 42 can penetrate below outer surface 44 of bone 12 in the above described manner ensures that lower surface 28 of body portion 24 is prevented from contacting outer surface 44 of bone 12 when fixation member 16 is biased against outer surface 44 of bone 12.

Having penetration structures 42 configured such that they only penetrate outer surface 44 of bone 12 to a limited degree is an important aspect of the present invention. In particular, the piercing of penetration structures 42 into outer surface 44 of bone 12 ensures that arm members 32 of fixation member 16 remain securely attached to bone fragments 14. Having arm members 32 securely attached to bone fragments 14 ensures that fixation member 16 functions to effectively inhibit relative movement between bone fragments 14 and thus enhances the healing of bone 12. On the other hand, limiting the penetration of penetration structures 42 ensures that a space 122 (see FIG. 2) is maintained between outer surface 44 of bone 12 and lower surface 28 of body portion 24. Having space 122 interposed between outer surface 44 and lower surface 28 ensures that an adequate blood supply is provided to bone 12. Ensuring that at an adequate blood supply is provided to bone 12 also enhances the healing of bone 12.

In contrast to the present invention, other mechanisms utilized to inhibit the relative movement between bone fragments either do not have (i) structures configured to penetrate the bone surface, and thus do not adequately immobilize the bone fragments, or (ii) penetrating structures which are configured so as to limit their penetration of the bone surface. Mechanism which do not have penetrating structures configured to limit the penetration thereof, allow the body portion (e.g. a plate) of the mechanism to come into contact with the bone surface. As discussed above, allowing the body or plate portion to come into contact with the bone can cause the blood supply of the bone to become occluded and thus inhibit healing. Therefore, based upon the above discussion it should be appreciated that the configuration of fixation member 16 provides significant advantages over other mechanisms utilized to immobilize bone fragments.

As shown in more detail in FIG. 15, fastener hole 52 has an edge 58 and a center as illustrated by center line 56. Edge 58 includes a convex wall portion 60 which extends towards center line 56. Convex wall portion 60 is configured to contact a convex wall segment 124 defined on screw 20 (see FIG. 2) when screw 20 is inserted through fastener hole 52 and utilized to secure fixation member 16 to bone 12. Having convex wall portion 60 serve as a bearing surface for convex wall segment 124 reduces the contact surface area between screw 20 and edge 58 as compared to having a flat edge acting as a bearing surface for a flat screw wall segment. Reducing the contact surface area between screw 20 and edge 58 reduces the probability that small pieces of metal or other material will be sheared off of edge 58 or convex wall segment 124 as screw 20 is rotated relative to, and biased against, edge 58.

Moreover, edge 58 further includes a land portion 62 secured to a lower end 64 of convex wall portion 60. Land portion 62 enhances the structural strength of body portion 24 in the area surrounding fastener hole 52. Furthermore, fastener hole 52 is eccentrically located relative to perpendicular central axis 38 of body portion 24. Having faster hole 52 eccentrically located relative to perpendicular central axis 38 cooperates with other features of fixation member 16 so as to allow a surgeon to secure fixation member 16 to a relatively large bone fragment 14 with screw 20 while still being able to reach smaller bone fragments 14 with penetration structures 42. In particular, as shown in FIGS. 1 and 2, having (i) an eccentrically located fastener hole 52 and (ii) arm members 32 of varying lengths allows fixation member 16 to be secured to a relatively large bone fragment 14 while still allowing penetration structures 42 to reach and secure relatively small bone fragments 16.

Still referring to FIG. 15, wire hole 66 is defined in body portion 24 such that wire hole 66 is spaced apart from fastener hole 52. Wire hole 66 is configured so that wire 22 can be inserted through wire hole 66 in a well known manner so as to stabilize fixation member 16 prior to securing fixation member 16 to bone 12 with screw 20.

Referring now to FIGS. 9, 10, 11, and 15, stop member 46 is connected to lower surface 28 of body portion 24. Stop member 46 is also configured to limit the penetration of penetration structures 42 so that lower surface 28 of body portion 24 is prevented from contacting outer surface 44 of bone 12 when fixation member 16 is biased against outer surface 44 of bone 12. In the exemplary embodiment shown in FIGS. 9, 10, 11, and 15, stop member 46 is an annular ridge 48 secured to a lower edge 127 of land portion 62 such that annular ridge 48 extends away from lower surface 28 of body portion 24. (Note securing annular ridge 48 in the above described manner results in annular ridge 48 being in a concentric relationship with fastener hole 52.) However, as discussed below, other structural configurations of stop member 46 are contemplated.

Stop member 46 (i.e. annular ridge 48) functions to prevent lower surface 28 of body portion 24 from coming into contact with outer surface 44 of bone 12 in the following manner. As fixation member 16 is urged against outer surface 44 of bone 12 (for example with screw 20), lower surface 28 is advanced toward outer surface 44 until an end surface 50 of annular ridge 48 contacts outer surface 44 of bone 12 whereupon the advancement of lower surface 28 toward outer surface 44 is stopped. Since annular ridge 48 extends outwardly from lower surface 28 a certain distance, space 122 is maintained between lower surface 28 and outer surface 44 of bone 12. Therefore, it should be appreciated that stop member 46 also prevents body portion 24 from coming into contact with outer surface 44 of bone 12 and thus ensures that an adequate blood supply is provided to bone 12.

It should also be appreciated that stop member 46 can be disposed on other areas of fixation member 16. For example, a stop member 46 can be disposed on penetration structures 42. Additionally, a stop member 46 could be disposed on each arm member 32 if desired. For example, it is contemplated that stop member 46 could be configured as a ridge extending from arm members 32. In this configuration a ridge is interposed between each penetration structure 42 and body portion 24 so as to limit the penetration of penetration structures 42. It should be further appreciated that fixation member 16 can be equipped with both (i) penetration structures 42 and (ii) stop member 46 so these elements can cooperate to prevent lower surface 28 of body portion 24 from coming into contact with outer surface 44 of bone 12. On the other hand, fixation member 16 can also be equipped with just penetration structures 42, or just stop member 46, since either one of these elements are sufficient to prevent lower surface 28 of body portion 24 from coming into contact with outer surface 44 of bone 12.

Referring now to FIGS. 3–8, 12, 13, and 14 there is shown three additional embodiments of fixation members (i.e. fixation members 18, 92, and 110) which can be used in the present invention. The aforementioned fixation members are substantially similar to fixation member 16. In addition, the aforementioned fixation members function, and have the same advantages, as discussed above with regard to fixation member 16. Furthermore, fixation members 18, 92, and 110 can be substituted for fixation member 16, or be used in conjunction with fixation member 16. Therefore, only a relatively brief description of these fixation members is provided below.

Figure 3:
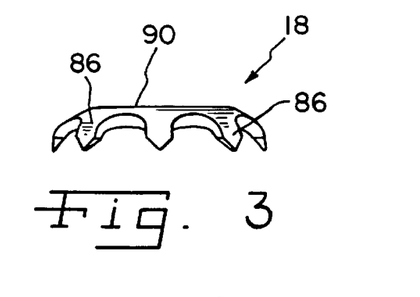
FIG. 3 is a side elevational view of a fixation member which can be used in the apparatus of FIG. 1.
Figure 4:
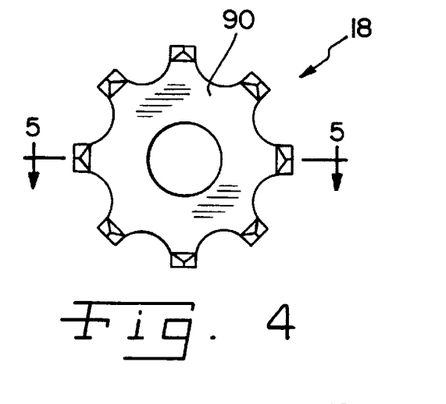
FIG. 4 is a bottom elevational view of the fixation member of FIG. 3.
Figure 5:
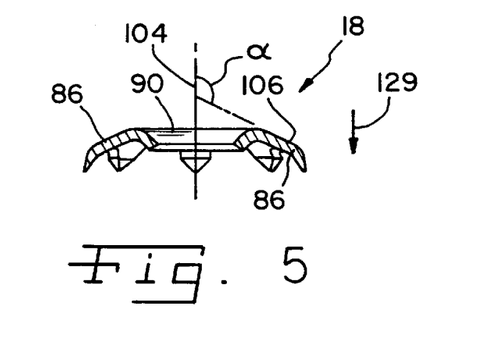
FIG. 5 is a cross-sectional view taken along the line 5—5 of FIG. 4 as viewed in the direction of the arrows.

Now referring to FIGS. 3, 4, and 5, fixation member 18 includes a body portion 90 and a number of arm members 86. In contrast to fixation member 16, fixation member 18 has a fastener hole which is concentric with a perpendicular central axis 104. In addition, fixation member 18 is structurally different from fixation member 16 in that fixation member 18 has arm members 86 which are angled downward relative to body portion 90 in the direction indicated by arrow 129. Furthermore, fixation member 18 does not include a stop member such as ridge 48 discussed above. With respect to the aforementioned angling, arm members 86 are angled relative to perpendicular central axis 104 such that a linear extension of a top surface 106 of arm members 86 defines an obtuse angle $\alpha$ between perpendicular central axis 104 and linear extension of top surface 106.

Figure 6:
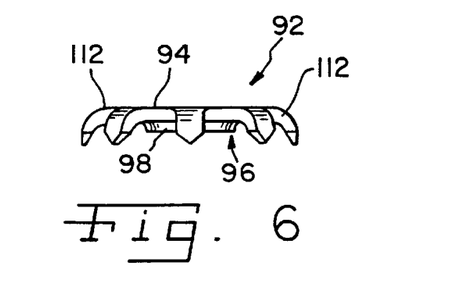
FIG. 6 is a side elevational view of another fixation member which can be used in the apparatus of FIG. 1.
Figure 7:
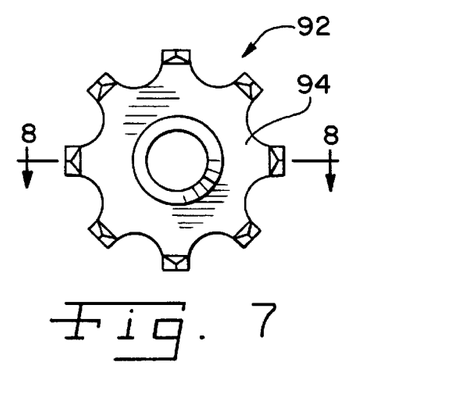
FIG. 7 is a bottom elevational view of the fixation member of FIG. 6.
Figure 8:
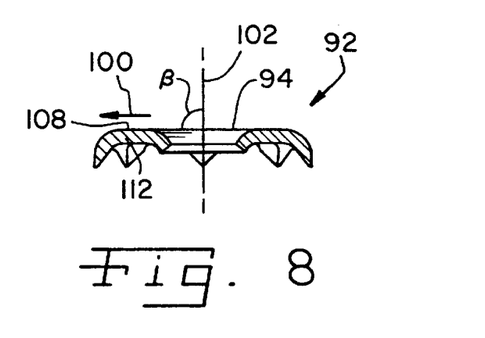
FIG. 8 is a cross-sectional view taken along the line 8—8 of FIG. 7 as viewed in the direction of the arrows.
Figure 9:
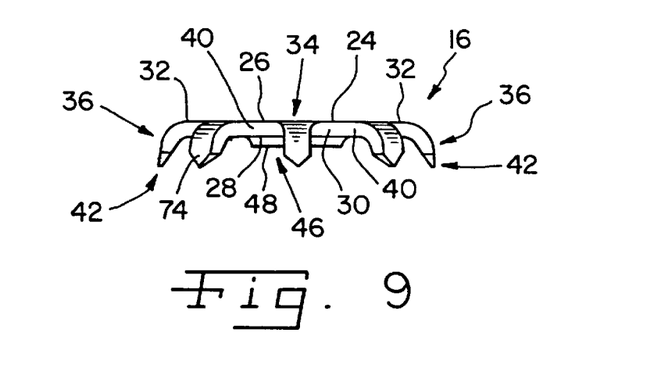
FIG. 9 is a side elevational view of another fixation member which can be used in the apparatus of FIG. 1.

Now referring to FIGS. 6, 7, and 8, fixation member 92 includes a body portion 94, a number of arm members 112, and a stop member 96 configured as an annular ridge 98. In contrast to fixation member 18, arm members 112 of fixation member 92 extend radially from body portion 94 in the direction indicated by arrow 100 such that a linear extension of a top surface 108 of each arm member 112 defines a right angle $\beta$ between the linear extension and a perpendicular central axis 102.

Figure 12:
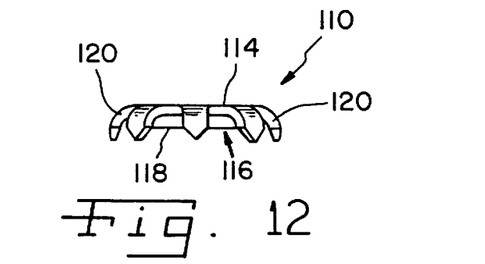
FIG. 12 is a side elevational view of yet another fixation member which can be used in the apparatus of FIG. 1
Figure 13:
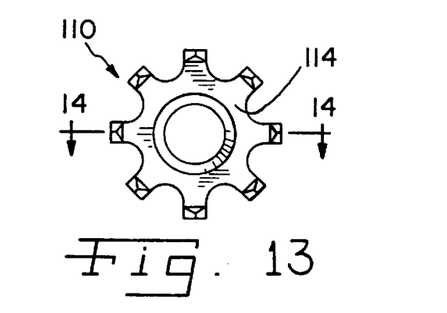
FIG. 13 is a bottom elevational view of the fixation member of FIG. 12.
Figure 14:
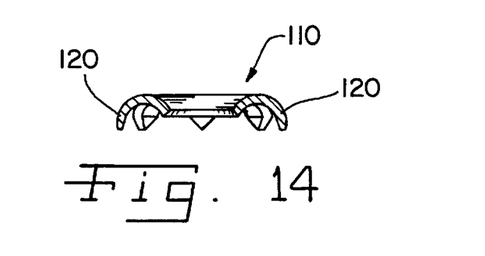
FIG. 14 is a cross-sectional view taken along the line 14—14 of FIG. 13 as viewed in the direction of the arrows.

Referring now to FIGS. 12, 13, and 14, fixation member 110 includes a body portion 114, a number of arm members 120, and a stop member 116 configured as an annular ridge 118. Arm members 120 of fixation member 110 radially extend from body portion 114 as previously discussed above for fixation members 18, 92, and 16, however each arm member 120 of fixation member 110 has an arcuate shape.

It should be understood that the above discussed different configurations of arm members 86, 112, and 120 allow fixation members 18, 92, and 110 to be utilized with different sized screws. In particular, fixation member 110 may be utilized with a relatively large screw, while fixation members 18 and 92 can be utilized with a relatively small screw.

Referring now to FIGS. 1 and 2, apparatus 10 can be used in the following manner. Initially a surgeon places fixation member 16 in an appropriate location on outer surface 44 of bone 12. In particular, fixation member 16 is positioned so that penetration structures 42 contact several bone fragments 14. Once fixation member 16 is positioned, an end of wire 22 is advanced through wire hole 66 while the other end of wire 22 is inserted into bone 12. Utilizing wire 22 in the aforementioned manner stabilizes fixation member 16 until screw 20 is inserted through fastener hole 52 and screwed into a bone fragment 14. Screwing screw 20 into bone fragment 14 causes fixation member 16 to be urged against outer surface 44 of bone 12 so that penetration structures 42 penetrate outer surface 44 in the previously described manner. Screwing screw 20 into bone fragment 14 also causes stop member 46 to contact outer surface 44 of bone 12. Thus, it should be appreciated that both penetration structures 42 and stop member 46 function to ensure that space 122 is maintained between body portion 24 and outer surface 44 of bone 12. Therefore, fixation member 16 effectively stabilizes bone fragments 14 while ensuring that an adequate flow of blood is provided to bone 12.

As shown in FIGS. 1 and 2, fixation member 16 can be used in conjunction with another fixation member, such as fixation member 18. Fixation member 18 is used in the same manner as described above for fixation member 16. Furthermore, wire 22 can be secured to both of the screws 20 used to fasten fixation members 16 and 18 so as to further stabilize bone fragments 14. Once both fixation members 16 and 18 are in place, wire 22 can be removed or left in place depending upon the surgeon's desire.

Based upon the above description it should be appreciated that the present invention provides fixation members which effectively stabilize bone fragments 14 of comminuted bone 12 without substantially occluding blood flow. In addition, the fixation members of the present invention are capable of stabilizing a plurality of bone fragments 14 without using a large number of screws 20. In particular, the fixation members of the present invention can stabilize a plurality of bone fragments 14 (including bone fragments 14 which are to small to have a screw 20 inserted therein) with the use of a single screw 20.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

What is claimed is:

1. A method of inhibiting relative movement between a first bone fragment and a second bone fragment, comprising the steps of:

advancing a fastener into said second bone fragment, said advancing step causing said fastener to contact a fixation member which in turn causes a first penetration structure of said fixation member to penetrate through an outer surface of said first bone fragment; and preventing further advancement of said penetration structure into said first bone fragment with a stop member of said fixation member so that a space is maintained between a lower surface of a body of said fixation member and said outer surface of said first bone fragment.

2. The method of claim 1, wherein said advancing step includes the step of advancing said fastener (i) through a fastener hole defined in said body of said fixation member, and (ii) into contact with a rim portion of said body of said fixation member, said rim portion being defined by said fastener hole.

3. The method of claim 1, wherein said preventing step includes the step of advancing said stop member into contact with said second bone fragment.

4. The method of claim 1, wherein:

said stop member includes an annular ridge which extends outwardly from said lower surface of said body of said fixation member, and said preventing step includes the step of advancing said annular ridge into contact with said second bone fragment after said penetration structure has penetrated through said outer surface of said first bone fragment.

5. The method of claim 3, wherein said stop member is disposed on said body of said fixation member.

6. The method of claim 3, wherein:

said fixation member further includes at least one arm extending outwardly from said body, and said stop member is disposed on said at least one arm.

7. The method of claim 1, wherein:

said fixation member further includes at least one arm extending outwardly from said body, and said penetration member is located on said arm.

8. The method of claim 6, wherein:

said fixation member includes a plurality of arms, each extending outwardly from said body, and said fixation member further includes a plurality of penetration structures, each being supported by a respective arm of said plurality of arms.

9. The method of claim 1, wherein:

said fixation member further includes at least one arm extending outwardly from said body, said stop member includes a ridge member which extends from said at least one arm, and said preventing step includes the step of advancing said ridge member into contact with said first bone fragment after said penetration structure has penetrated through said outer surface of said first bone fragment.

10. A method of inhibiting relative movement between a first bone fragment and a second bone fragment, comprising the steps of:

advancing a fastener into said second bone fragment, said fastener advancing step causing said fastener to move into contact with said fixation member; and advancing a first penetration structure of said fixation member through an outer surface of said first bone fragment in response to said fastener advancing step, wherein movement of said fastener into contact with said fixation member causes a stop member to contact either said first bone fragment or said second bone fragment so that (i) further advancement of said penetration structure through said outer surface of said first bone fragment is prevented, and (ii) a space is maintained between a lower surface of a body of said fixation member and said outer surface of said first bone fragment.

11. The method of claim 10, wherein said fastener advancing step includes the step of advancing said fastener (i) through a fastener hole defined in said body of said fixation member, and (ii) into contact with a rim portion of said body of said fixation member, said rim portion being defined by said fastener hole.

12. The method of claim 10, wherein:

said stop member includes an annular ridge which extends outwardly from said lower surface of said body of said fixation member, and movement of said fastener into contact with said fixation member causes said annular ridge to advance into contact with said second bone fragment after said penetration structure is advanced through said outer surface of said first bone fragment.

13. The method of claim 10, wherein:

said fixation member includes at least one arm extending outwardly from said body, said stop member includes a ridge member which extends from said at least one arm, and movement of said fastener into contact with said fixation member causes said ridge member to advance into contact with said first bone fragment after said penetration structure penetrates through said outer surface of said first bone fragment.

14. A method of stabilizing bone fragments, comprising the steps of:

advancing a fastener into contact with a fixation member;

advancing a penetration structure of said fixation member through an outer surface of a first bone fragment in response to said fastener advancing step, and moving a stop member of said fixation member into contact with either said first bone fragment or a second bone fragment, in response to said fastener advancing step, so that (a) further penetration of said penetration structure into said first bone fragment is prevented after said penetration structure has penetrated through said outer surface of said first bone fragment, and (b) a space is maintained between a lower surface of a body of said fixation member and said outer surface of said first bone fragment.

15. The method of claim 14, wherein said fastener advancing step includes the step of advancing said fastener (i) through a fastener hole defined in said body of said fixation member, and (ii) into contact with a rim portion of said body of said fixation member, said rim portion being defined by said fastener hole.

16. The method of claim 14, wherein:

said stop member includes an annular ridge which extends outwardly from said lower surface of said body of said fixation member, and movement of said fastener into contact with said fixation member causes said annular ridge to advance into contact with said second bone fragment after said penetration structure is advanced through said outer surface of said first bone fragment.

17. The method of claim 14, wherein:

said fixation member includes at least one arm extending outwardly from said body, said stop member includes a ridge member which extends from said at least one arm, and movement of said fastener into contact with said fixation member causes said ridge member to advance into contact with said first bone fragment after said penetration structure is advanced through said outer surface of said first bone fragment.

18. The method of claim 14, wherein:

said stop member is disposed on said body of said fixation member, and said fixation member further includes a plurality of arms extending outwardly from said body.

19. The method of claim 14, wherein:

said fixation member includes at least one arm extending outwardly from said body, and said stop member is disposed on said at least one arm.

20. The method of claim 14, wherein:

said fixation member includes a plurality of arms, each extending outwardly from said body, and said fixation member further includes a plurality of penetration structures, each being supported by a respective arm of said plurality of arms.

* * * * *